US011045194B2

(12) United States Patent
King et al.

(10) Patent No.: US 11,045,194 B2
(45) Date of Patent: Jun. 29, 2021

(54) COMPRESSIVE COUPLER FOR RELOADABLE HEMOSTASIS CLIPPING DEVICE

(71) Applicant: BOSTON SCIENTIFIC SCIMED, INC., Maple Grove, MN (US)

(72) Inventors: Joseph W King, Franklin, MA (US); Shawn Ryan, Littleton, MA (US); Laurie A. Lehtinen, Marlborough, MA (US); Daniel Congdon, Wenham, MA (US); Ramon Estevez, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 459 days.

(21) Appl. No.: 15/832,462

(22) Filed: Dec. 5, 2017

(65) Prior Publication Data
US 2018/0153552 A1    Jun. 7, 2018

Related U.S. Application Data

(60) Provisional application No. 62/430,453, filed on Dec. 6, 2016.

(51) Int. Cl.
*A61B 17/08* (2006.01)
*A61B 17/128* (2006.01)
(Continued)

(52) U.S. Cl.
CPC .......... *A61B 17/083* (2013.01); *A61B 17/128* (2013.01); *A61B 17/12009* (2013.01);
(Continued)

(58) Field of Classification Search
CPC . A61B 17/083; A61B 17/1285; A61B 17/128; A61B 17/12009;
(Continued)

(56) References Cited

U.S. PATENT DOCUMENTS 8,062,311 B2    11/2011   Litscher et al.
8,080,021 B2    12/2011   Griego
(Continued)

FOREIGN PATENT DOCUMENTS

CN      104546055       4/2015
EP       2380509       10/2011
(Continued)

*Primary Examiner* — Tan-Uyen T Ho
*Assistant Examiner* — Rachel S Highland
(74) *Attorney, Agent, or Firm* — Fay Kaplun & Marcin, LLP (57) ABSTRACT

A system for treating tissue includes a clip assembly including a pair of clip arms, proximal ends of which are slidably received within a channel of a capsule to be moved between a tissue receiving configuration, in which distal ends of the clip arms are separated from one another, and a tissue clipping configuration, in which the distal ends are moved toward one another. The system also includes an applicator including a catheter and a control member extending therethrough. The control member configured to be connected to the clip arms to move the clip assembly between the tissue receiving and tissue clipping configurations. The system also includes a coupler attached to one of a proximal end of the capsule of the clip assembly and a distal end of the catheter, and configured to releasably couple the capsule and the catheter to one another.

12 Claims, 7 Drawing Sheets

(51) Int. Cl.
*A61B 17/12* (2006.01)
*A61B 17/122* (2006.01)
*A61B 17/00* (2006.01)

(52) U.S. Cl.
CPC ........ *A61B 17/1285* (2013.01); *A61B 17/122* (2013.01); *A61B 17/1227* (2013.01); *A61B 2017/0046* (2013.01); *A61B 2017/00473* (2013.01); *A61B 2017/12004* (2013.01)

(58) Field of Classification Search
CPC ...... A61B 2017/00473; A61B 17/1227; A61B 2017/12004; A61B 17/122; A61B 2017/0046
See application file for complete search history.

(56) References Cited

U.S. PATENT DOCUMENTS

| | | | |
|---|---|---|---|
| 9,959,977 B2 | 5/2018 | Wada et al. | |
| 2007/0282355 A1* | 12/2007 | Brown | A61B 17/122 606/151 |
| 2008/0306491 A1 | 12/2008 | Cohen et al. | |
| 2009/0275959 A1* | 11/2009 | Cui | A61B 17/122 606/143 |
| 2014/0088616 A1 | 3/2014 | Clerc et al. | |
| 2015/0173768 A1* | 6/2015 | Wells | A61B 17/122 606/142 |

FOREIGN PATENT DOCUMENTS

| | | |
|---|---|---|
| JP | 2009/125547 | 6/2009 |
| JP | 2013-544127 | 12/2013 |
| JP | 2015-532859 | 11/2015 |

\* cited by examiner

COMPRESSIVE COUPLER FOR RELOADABLE HEMOSTASIS CLIPPING DEVICE

PRIORITY CLAIM

This present disclosure claims priority to U.S. Provisional Patent Application Ser. No. 62/430,453 filed Dec. 6, 2016; the disclosure of which is incorporated herewith by reference.

BACKGROUND INFORMATION

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present embodiments are directed to a system for treating tissue, comprising a clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another and an applicator including a catheter and a control member extending therethrough, the control member including a distal end configured to be connected to the clip arms to move the clip assembly between the tissue receiving configuration and the tissue clipping configuration, and a coupler attached to one of a proximal end of the capsule of the clip assembly and a distal end of the catheter of the applicator, the coupler configured to releasably couple the capsule and the catheter to one another.

In an embodiment, the proximal ends of the clip arms may be connected to one another via a yoke releasably coupleable with an enlarged distal end of the control member.

In an embodiment, the coupler may be attached to the proximal end of the capsule and a proximal portion of the coupler may include a plurality of arms mountable over a distal portion of the catheter to be releasably coupled thereto, the arms movable between a biased engaging configuration and a non-engaging configuration, in which the arms are deflected away from a longitudinal axis of the coupler.

In an embodiment, each of the arms may include a groove extending along an interior surface thereof, the groove sized and shaped to receive a correspondingly sized and shaped tab extending outwardly laterally away from the distal end of the catheter.

In an embodiment, the groove may include a tapered surface tapering toward a distal end thereof so that when a compressive force is applied to the coupler, the tab of the catheter slides distally along the tapered surface of the groove to deflect the arms away from the longitudinal axis of the coupler.

In an embodiment, a proximal interior edge of each of the arms may be angled.

In an embodiment, the catheter may include a shoulder extending along a portion thereof for interfacing with the proximal edge of the arms to deflect the arms away from the longitudinal axis.

In an embodiment, the coupler may further include a plurality of fingers coupled to the proximal end of the capsule, a distal end of each of the fingers including a tab extending radially inward to engage a correspondingly sized and shaped window extending laterally through a wall of the proximal portion of the capsule.

In an embodiment, the window may be elongated to permit a longitudinal sliding of the coupler relative to the capsule.

In an embodiment, the coupler may further include a plurality of fingers coupled to the proximal end of the capsule, a distal end of each of the fingers including a tab extending radially inward to engage a correspondingly sized and shaped window extending laterally through a wall of the proximal portion of the capsule.

In an embodiment, an interior surface of each of the fingers may include a ramped surface tapering toward a proximal end thereof so that when a compressive force is applied thereto, the fingers deflect away from a longitudinal axis of the coupler.

The present embodiments are also directed to a reloadable clipping device, comprising a clip assembly including a pair of clip arms, each of the clip arms extending from a proximal end to a distal end, the proximal end of each of the clip arms connected to one another via a yoke slidably received within a channel of a capsule and configured to be connected to a control member of an applicator, and a coupler attached to a proximal end of the capsule and configured to be coupled to an applicator so that the clip arms are movable relative to the capsule via the applicator between a tissue receiving configuration, in which distal ends of the clip arms are separated from one another, and a tissue clipping configuration, in which distal ends of the clip arms are moved toward one another to move the clip assembly between the tissue receiving configuration and the tissue gripping configuration.

In an embodiment, a proximal portion of the coupler may include a plurality of arms mountable over a distal portion of the catheter to be releasably coupled thereto, the arms movable between a biased engaging configuration and a non-engaging configuration, in which the arms are deflected away from a longitudinal axis of the coupler.

In an embodiment, each of the arms may include a groove extending along an interior surface thereof, the groove sized and shaped to receive a correspondingly sized and shaped engaging feature extending outwardly laterally away from the distal end of the catheter.

In an embodiment, the groove may include a tapered surface tapering toward a distal end thereof.

In an embodiment, the coupler may be configured to yield when a compressive force is applied thereto, the engaging feature of the catheter sliding distally along the tapered surface of the groove to deflect the arms away from the longitudinal axis of the coupler.

The exemplary embodiments are also directed to a method for treating tissue, comprising loading a clip assembly on an applicator by coupling a control member of the applicator to clip arms of the clip assembly and by coupling a catheter of the applicator to a capsule of the clip assembly via a coupler that is attached to a proximal end of the capsule, inserting the loaded clip assembly to a target site within a living body via a working channel of an endoscope, moving the clip assembly between a tissue receiving configuration, in which distal ends of the clip arms are separated from one another, and a tissue clipping configuration, in which distal ends of the clip arms are moved toward one another, by moving the control member longitudinally relative to the catheter until target tissue is gripped therebetween, locking the clip arms relative to the capsule in the tissue gripping configuration, and deploying the clip assembly from the applicator by drawing the control member proximally relative to the clip arms, until a compressive force on the coupler exceeds a predetermined threshold value, so that the coupler yields to release the catheter therefrom, and the control member is disengaged from the clip arms.

BRIEF DISCLOSURE

DETAILED DESCRIPTION

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the clipping system includes a coupler for releasably coupling a capsule of the clip assembly with a catheter of the applicator. The coupler may be pre-assembled with one of the capsule and the catheter and configured to be coupled to the other of the capsule and the catheter. When it is desired to deploy the clip assembly in the body, a compressive force on the coupler causes the coupler to fracture and/or yield to disengage the capsule from the catheter.

Figure 1:
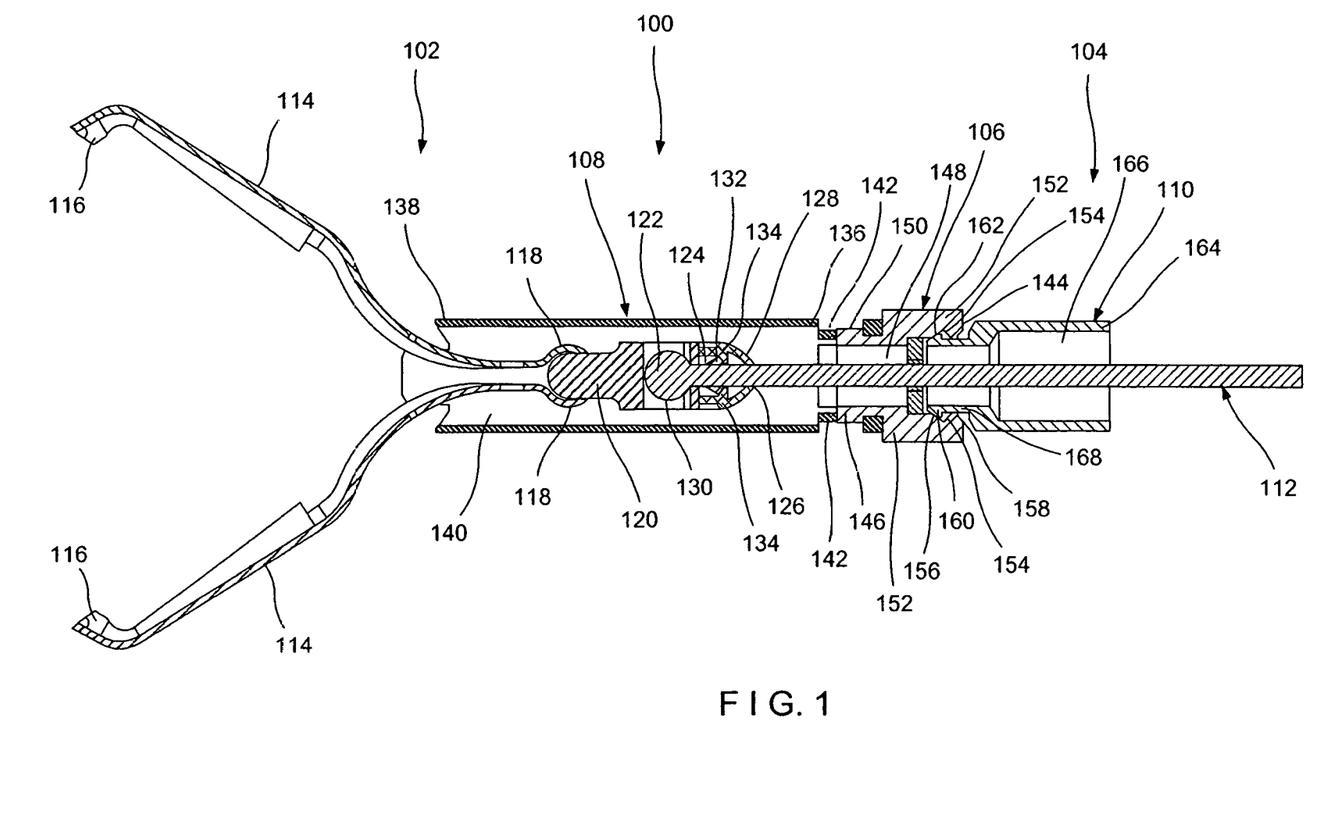
FIG. 1 shows a longitudinal cross-sectional view of a system according to an exemplary embodiment of a present disclosure.

As shown in FIG. 1, a system 100 according to an exemplary embodiment of the present disclosure comprises a clipping assembly 102, an applicator 104 and a coupler 106 facilitating a releasable connection between the applicator 104 and the clipping assembly 102. The clip assembly 102 is loadable onto an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. In this embodiment, a capsule 108 of the clip assembly 102 is pre-assembled with the coupler 106 and is configured to be releasably connected to a catheter 110 of the applicator 104. Once the capsule 108 of the clip assembly 102 has been coupled to the catheter 110 of the applicator 104, a control member 112 of the applicator 104 releasably connected to clip arms 114 of the clip assembly 102 may be moved longitudinally relative to the catheter 110 and capsule 108 to move the clip assembly 102 between an open tissue receiving configuration, in which distal ends 116 of the clip arms 114 are separated from one another to receive target tissue therebetween, and a closed tissue gripping configuration, in which the distal ends 116 are drawn toward one another to grip target tissue therebetween. Upon clipping of the target tissue, as desired, a compressive force may be exerted on the coupler 106 causing portion of the coupler 106 to yield and/or fracture to release the catheter 110 from the capsule 108. It is noted that although this exemplary embodiment is shown and described with a coupler 106 pre-assembled with the capsule 108 of the clip assembly 102, in another embodiment, the coupler 106 may be similarly pre-assembled with the catheter 110 of the applicator 104 to be releasably connected to the capsule 108.

The clip assembly 102 includes a pair of clip arms 114, proximal ends 118 of which are connected to a yoke 120 slidably received within the capsule 108 so that, when the yoke 120 is coupled to the control member 112 of the applicator 104 and the capsule 108 is coupled to the catheter of the applicator 104 via the coupler 106, longitudinal motion of the control member 112 relative to the catheter 110 moves the clip assembly 102 between the tissue receiving and the tissue gripping configurations. The clip arms 114 of this embodiment are biased toward the open tissue receiving configuration so that, when not constrained by the capsule 108, the clip arms 114 move under their natural bias to the tissue receiving configuration with distal ends 116 of the clip arms 114 spread apart from one another. When the clip arms 114 are drawn into the capsule 108, the capsule 108 constrains the clip arms 114, holding the distal ends 116 together in the tissue gripping configuration.

Each of the clip arms 114 extends from a proximal end 118 to a distal end 116. As would be understood by those skilled in the art, the clip arms 114 may include optional gripping features configured to enhance the gripping of tissue therebetween. For example, the distal ends 116 of one or both of the clip arms 114 may include tips extending laterally inward toward the other clip arm 114 with the tips including, for example, teeth, protrusions, spikes or other structures) configured to grip tissue between the distal ends 116. One or both of the clip arms 114 may also include a locking feature configured to lock the clip arms 114 in the tissue gripping configuration after target tissue has been gripped as desired by the clip arms 114. In one embodiment, one or both of the clip arms 114 includes a locking tab extending laterally outward therefrom configured to engage a portion of the capsule 108 when the clip arms 114 have been drawn into the capsule 108 by a predetermined distance. For example, the locking tabs may be received within correspondingly sized, shaped and positioned locking windows extending laterally into or through a wall of the capsule 108 to lock the clip arms 114 relative to the capsule 108, in the tissue gripping configuration.

In one embodiment, the proximal ends 118 of the clip arms 114 are connected to one another to form one integral piece which is connected to the yoke 120. In another embodiment, the proximal ends 118 are connected to one another via the yoke 120. The yoke 120 is connected to the proximal ends 118 of the clip arms 114 and is configured to be releasably connected to an enlarged distal end 122 of the control member 112 of the applicator 104. For example, the yoke 120 may include a longitudinal slot 124 extending from a proximal opening 126 at a proximal end 128 of the yoke 120 along a longitudinal axis of the yoke 120 to a distal portion 130 sized and shaped to receive the enlarged distal end 122 of the control member 112 of the applicator 104. In one exemplary embodiment, the enlarged distal end 122 is configured as a ball received within a correspondingly sized and shaped socket of the distal portion 130. A proximal portion 132 of the slot 124 extending between the proximal opening 126 and the distal portion 130 has a cross-sectional area (e.g., diameter) smaller than a cross-sectional area of the distal portion 130. The slot 124 may be defined via opposed portions 134 that are spreadable to receive the enlarged distal end 122 and are biased toward one another so that, once the enlarged distal end 122 passes distally into the distal portion 130, the opposed portions 134 spring back to lock the enlarged distal end 122 within the distal portion 130, coupling the control member 112 to the yoke 120. Thus, longitudinal movement of the control member 112 relative to the capsule 108 controls movement of the clip arms 114 between the tissue receiving and the tissue clipping configurations.

According to this embodiment, the enlarged distal end 122 of the control member 112 may be inserted into the distal portion 130 via the proximal opening 126 of the yoke 120. When the control member 112 is pushed distally into the yoke 120 beyond a predetermined threshold value, the proximal opening 126 of the slot 124 deforms via separation of the opposed portions 134 to permit the enlarged distal end 122 to pass through the proximal portion 132 into the distal portion 130. Once the enlarged end 122 is received within the distal portion 130, the proximal portion 132 of the slot 124 reverts to its original size, holding the enlarged end 122 of the control member 112 in the distal portion 130.

The capsule 108 extends from a proximal end 136 to a distal end 138 and includes a channel 140 extending longitudinally therethrough. The channel 140 is sized and shaped to slidably receive the yoke 120 and at least a proximal portion of the clip arms 114 therein. As described above, the capsule 108 may also include locking features (e.g., locking windows) for engaging corresponding locking features of the clip arms 114 (e.g., locking tabs). In this embodiment, the proximal end 136 may be pre-assembled with the coupler 106. The capsule 108 may include a window 142 extending laterally through the proximal end 136 thereof for receiving a correspondingly sized and shaped engaging feature of the coupler 106. In one embodiment, the capsule 108 may include a pair of diametrically opposed windows 142 for engaging the coupler 106. It will be understood by those of skill in the art, however, that the capsule 108 may include any number of windows 142 for receiving any number of corresponding engaging features of the coupler 106. It will also be understood by those of skill in the art that the coupler 106 may be pre-assembled with the capsule 108 via any one of a variety of couplings. In another example, laterally extending tabs on the proximal end 136 of the capsule 108 may be received within correspondingly sized and shaped windows of the coupler 106. In another example, the coupler 106 may be press fit onto the capsule 108 and/or adhered thereto via an adhesive.

The coupler 106 extends from a proximal end 144 to a distal end 146 and includes a channel 148 extending therethrough. The distal end 146 of the coupler 106 may be pre-assembled with the proximal end 136 of the capsule 108 so that the channel 148 of the coupler 106 is in communication with the channel 140 of the capsule 108. Thus, the control member 112 of the applicator 104 may be passed through the channels 148, 140 of the coupler 106 and the capsule 108, respectively, to be coupled to the yoke 120 during loading of the clip assembly 102. A distal portion of the coupler 106 may be sized and shaped to be received within the channel 140 of the capsule 108 so that outwardly extending lateral tabs 150 at the distal end 146 of the coupler 106 may be received within the windows 142 of the capsule 108 to connect the coupler 106 thereto. In one embodiment, the coupler 106 may include a pair of opposing tabs 150 received within diametrically opposing windows 142 of the capsule 108. The coupler 106, however, may include any number of tabs 150 for connecting the coupler 106 to the capsule 108. Although the coupler 106 is described and shown as a separate element connected to the capsule 108, in an alternate embodiment, the coupler 106 may be integrally formed with the capsule 108.

A proximal portion of the coupler 106 of this embodiment includes a plurality of arms 152 configured to engage the catheter 110 of the applicator 104. The arms 152 are mounted over a distal end 160 of the catheter 110 so that the catheter 110 and the coupler 106 are snap fit together. The arms 152 are biased toward an engaging configuration, but may be spread apart to permit the distal end 160 of the catheter 110 to be received therein. In particular, each of the arms 152 includes a groove 154 extending along an interior surface thereof, the groove 154 sized and shaped to receive a corresponding engaging feature 162 of at the distal end 160 of the catheter 110. The arms 152 deflect away from one another as the engaging features 162 at the distal end 160 are being inserted therebetween. Once the engaging features 162 are received within the grooves 154, however, the arms 152 snap inward under their natural bias so that the grooves 154 and the engaging features 162 engage one another, coupling the catheter 110 to the coupler 106. Each of the grooves 154 of this embodiment includes a tapered surface 156 tapering toward a distal end thereof. As will be described in further detail below, the tapered surfaces 156 are configured to interface with the engaging features 162 when a compressive force is applied thereto, causing the coupler to yield to release the catheter 110 therefrom. A proximal interior edge 158 of each of the arms 152 may also be angled, tapering toward a distal end thereof so that, when a portion of the coupler 106 comes into contact therewith, a further force may be exerted on the coupler 106.

The applicator 104 includes the catheter 110, a flexible member (not shown) extending proximally therefrom, and the control member 112 extending longitudinally through the flexible member and the catheter 110. A proximal end of the flexible member may be connected to a handle portion.

A proximal end of the control member 112 may be connected to an actuator of the handle portion so that the longitudinal movement of the control member 112 relative to the flexible member and catheter 110 may be controlled by a user at the handle portion. The flexible member may be formed as a coil or wire having sufficient flexibility to be passed through even tortuous paths of the living body and, in this embodiment, is sized and shaped to be passed through a working channel of an endoscope or other insertion device. The flexible member, however, may be formed of any other suitable flexible structure so long as the flexible member is capable of providing a force in compression sufficient to counter the tension to be placed on the control member 112 from the clip assembly 102.

The catheter 110 extends longitudinally from a proximal end 164 connected to the flexible member to the distal end 160 configured to be releasably coupled to the coupler 106. The control member 112 extends through a lumen 166 of the catheter 110. A distal portion 168 of the catheter 110 may be sized and shaped to be inserted between the arms 152 of the coupler 106 so that engaging features 162 at the distal end 160 of the catheter 110 are received and engaged with the grooves 154. In one embodiment, the engaging features 162 may be configured as tabs extending laterally outward (e.g., extending away from a longitudinal axis of the catheter 110) from the distal end 160. The tabs of the engaging features 162 may be sized and shaped to correspond to the grooves 154 so that when the tabs may be received with the grooves 154 via a snap fit.

When it is desired to disengage the catheter 110 from the coupler 106 to deploy the clip assembly 102 in the body, a compressive force may be applied to the coupler 106 by drawing the control member 112 proximally relative thereto. Once the clip assembly 102 is locked in the tissue gripping configuration, proximal motion of the control member 112 draws the entire clip assembly 102, including the coupler 106 coupled thereto, proximally. The coupler 106 is thus drawn proximally against the catheter 110 and the engaging features 162 slide distally along the tapered surfaces 156 of the grooves 154, deflecting the arms 152 radially outward to disengaging the coupler 106 from the catheter 110. In a further embodiment, a further proximal movement of the coupler 106 may cause a shoulder 170 of the catheter 110, immediately proximal of the distal portion 168, to engage the proximal edge 158, causing the arms 152 to deflect even more. In one embodiment, the coupler 106 may yield by deflecting the arms 152 away from the longitudinal axis so that the grooves 154 disengage the engaging features 162 of the catheter 110. In another embodiment, deflection of the arms 152 may cause the coupler 106 to fracture, thereby releasing the catheter 110 therefrom.

Prior to being loaded on the applicator 104, the clip assembly 102 (with the coupler 106 pre-assembled therewith) may be stored in a cartridge configured to facilitate loading of the clip assembly 102 on the applicator 104. The cartridge may be configured as a storage container defining a space therewithin that is sized and shaped to house the clip assembly 102 with the coupler 106. The clip assembly 102 may be housed within the cartridge in the tissue receiving configuration. The cartridge includes a proximal opening through which the distal portion of the applicator 104 may be inserted to be coupled to the clip assembly 102, as will be described in further detail below. The cartridge holds the clip assembly 102 in position to facilitate loading onto the applicator 104.

An exemplary method for loading the clip assembly 102 onto the applicator 104 comprises coupling the control member 112 to the clip arms 114 and coupling the catheter 110 to the capsule 108 via the coupler 106. The enlarged distal end 122 of the control member 112 may be coupled to the clip arms 114 via the yoke 120 by pushing the enlarged distal end 122 distally against the proximal opening 126 of the yoke 120 until a distal force exerted thereon exceeds a predetermined threshold value, causing opposed portions 134 thereof to deflect away from one another to permit the enlarged distal end 122 to be moved distally therepast into the distal portion 130 of the longitudinal slot 124. Once the enlarged distal end 122 is received within the distal portion 130, the opposing portions 134 revert to their original position, holding the enlarged distal end 122 within the yoke 120. The catheter 110 may be coupled to the capsule 108 via the coupler 106 by inserting the distal portion 168 between the arms 152 of the coupler 106 so that the coupler 106 and the catheter 110 engage one another via a snap fit. In particular, engaging features 162 of the catheter 110 are received within the grooves 154 of the arms 152 of the coupler 106.

As described above, where the clip assembly 102 is housed within a cartridge, the distal portion 168 of the catheter 110 and the enlarged distal end 122 of the control member 112 may be inserted through a proximal opening of the cartridge to be coupled to the clip assembly 102, in substantially the same manner as described above. Once the catheter 110 has been releasably connected to the capsule 108 and the enlarged distal end 122 is coupled to the clip arms 114, the control member 112 may be moved proximally to draw the clip assembly 102 toward the closed, clipping configuration. The entire applicator 104 may then be moved proximally relative to the cartridge to draw the clip assembly 102 out of the cartridge, in the closed configuration, via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the tissue gripping configuration to reduce damage and facilitate its passage through the working channel. Upon reaching the site of the target tissue, the clip assembly 102 is advanced out of the distal end of the working channel by moving the control member 112 distally relative to the catheter 110, extending the clip arms 114 distally out of the capsule 108 and moving the clip arms 114 to the tissue receiving configuration. Once the target tissue has been received between the clip arms 114, the clip assembly 102 may be moved toward the tissue gripping configuration so that the target tissue is gripped between the distal ends 116 thereof. The clip arms 114 are moved toward the tissue gripping configuration by drawing the control member 112 proximally with respect to the catheter 110 and the capsule 108. Once the clip assembly 102 is in the tissue gripping configuration, the control member 112 may be drawn further proximally to lock the clip arms 114 with respect to the capsule 108.

To deploy the clip assembly 102, the control member 112 may be drawn further proximally until the coupler 106 attached to the capsule 108 drawn proximally against the catheter 110. The proximal motion of the coupler 106 causes the engaging features 162 of the catheter 110 to slide distally against the tapered surfaces 156 of the grooves 154, thereby deflecting the arms 152 radially outward, out of engagement with the engagement features 162. In a further embodiment, the coupler 106 may be moved even further proximally relative to the catheter 110, causing the shoulder 170 of the catheter 110 to interface with the proximal edge 158 resulting in even further deflection of the arms 152. As described above, the coupler 106 may yield and/or fracture to release the catheter 110 therefrom.

Once the catheter 110 has disengaged from the coupler 106, the control member 112 is drawn even further proximally until the enlarged distal end 122 disengages from the yoke 120. In particular, when the force exerted on the yoke 120 by the enlarged distal end 122 exceeds a predetermined threshold value, opposed portions 134 spread apart, releasing the enlarged distal end therefrom. Alternatively, the yoke 120 may fracture to release the clip assembly 102 from the control member 112. The entire applicator 104—including the control member 112 and the catheter 110—may then be withdrawn proximally from the body, leaving the clip assembly 102 (and any portions of the coupler 106 remaining attached thereto) clipped over the target tissue. Where the coupler 106 fractures to release the catheter 110 therefrom, any portions of the coupler 106 that break off may be left in the body to pass naturally through the GI tract. If so desired, a new clip assembly 102 is then loaded onto the applicator 104, in the same manner as described above, so that the system 100 may then be used to clip a second portion of tissue. This process may be repeated using the same applicator 104 as many times as needed or desired.

Figure 2:
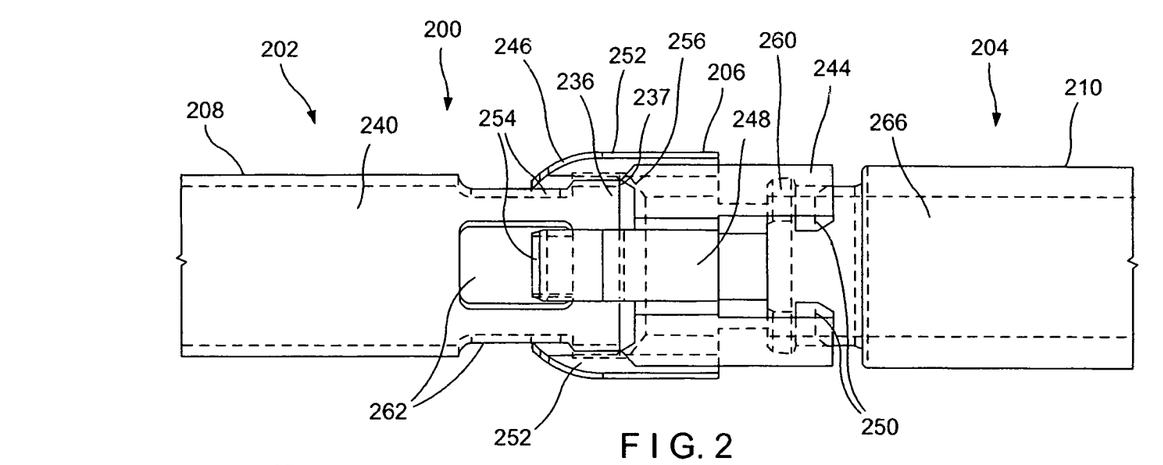
FIG. 2 shows a longitudinal side view of a system according to another exemplary embodiment of the present disclosure.
Figure 3:
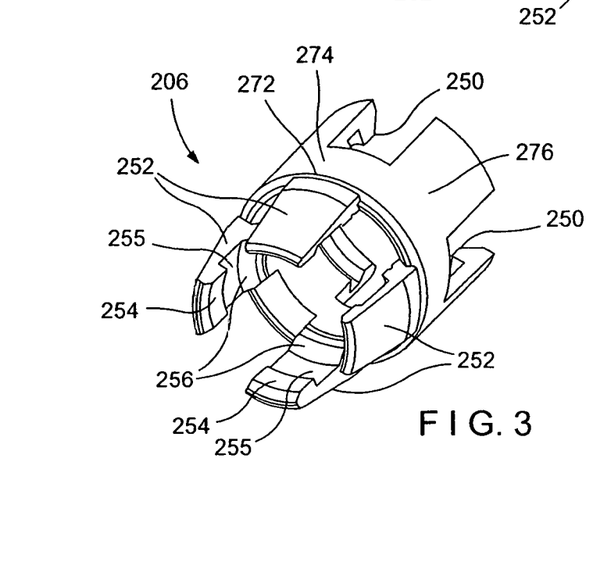
FIG. 3 shows a perspective view of a coupler of the system of FIG. 2.
Figure 4:
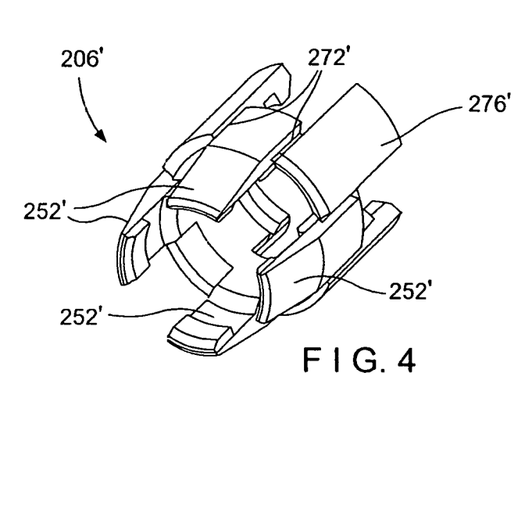
FIG. 4 shows a perspective view of a coupler according to an alternate embodiment of the present disclosure.

As shown in FIGS. 2-4, a system 200 according to another exemplary embodiment of the present disclosure is substantially similar to the system 100 described above, comprising a clip assembly 202, an applicator 204 and a coupler 206 facilitating a releasable connection between the applicator 204 and the clip assembly 202. The clip assembly 202 is substantially similar to the clip assembly 102 including a pair of clip arms (not shown), proximal ends of which are connected to a yoke (not shown) slidably received within a channel 240 of a capsule 208. The applicator 204 is substantially similar to the applicator 104, including a catheter 210 attached to a distal end of a flexible member (not shown) and a control member (not shown) extending therethrough. In this embodiment, the coupler 206 is pre-assembled with the capsule 208.

The coupler 206 extends from a proximal end 244 to a distal end 246 and includes a channel 248 extending therethrough. The distal end 246, in this embodiment, may be pre-assembled with a proximal end 236 of the capsule 208. A distal portion of the coupler 206 includes a plurality of fingers 252 mounted over the proximal end 236 of the capsule 208. Distal ends 246 of each of the fingers 252 include an engaging feature 254 for engaging a corresponding engaging feature 262 of the capsule 208. In one embodiment, the engaging feature 254 of the fingers 252 may include a radially inwardly extending tab that is received within a correspondingly sized and shaped window (engaging feature 262) extending laterally through a wall of the capsule 208 at the proximal end thereof. Although the exemplary embodiment shows and describes a tab received within a window, the engaging feature 254 of the coupler 206 and the engaging feature 262 of the capsule 208 may have any of a variety of configurations so long as the engaging features 254, 262 engage one another.

The proximal end 244 of the coupler 206 is configured to be coupled to a distal end 260 of the catheter 210 in any of a number of ways. In one embodiment, a proximal portion of the coupler 206 may include a plurality of deflectable arms 276, which may be mounted over the distal end 260 of the catheter 210. Each of the arms 276 may include a plurality of tabs 250 extending radially inward to engage a corresponding portion of the catheter 210. The distal end 260 of the catheter 210 may, for example, include a plurality of correspondingly sized and shaped windows or grooves for receiving the plurality of tabs 250 therein. The arms 276 in this embodiment are biased toward an engaging configuration and may be spread apart to permit the distal end 260 of the catheter 210 to be received therebetween. When it is desired to couple the applicator 204 to the clip assembly 202, the distal end 260 of the catheter 210 may be pushed distally against the proximal end 244 of the coupler 206 until the arms 276 deflect away from one another as the distal end 260 is received therebetween. In this embodiment, each of the tabs 250 includes an angled surface so that, when the distal end 260 of the catheter 210 is pushed thereagainst, the tabs 250 slide therealong with the arms 276 moving radially outward. Once the tabs 250 are received within the windows/grooves of the catheter 210, the arms 276 revert to their biased configurations so that the engaging features 252 engage the catheter 210. The coupler 206 is coupled to the catheter 210 so that the channel 248 of the coupler 206 is in communication with a lumen 266 of the catheter 210 and so that the control member may be moved longitudinally through the coupler 206 until an enlarged distal end of the control member extends distally past the distal end of the coupler 206 to engage the yoke of the clip assembly 202.

The coupler 206 is configured to release the capsule 208 therefrom while remaining engaged to the catheter 210 when deploying the clip assembly 202 in the body. In particular, an interior surface 255 of each of the fingers 252 includes a ramped surface 256 tapering toward the proximal end 244 of the coupler 206. The ramped surface 256 of each of the fingers 252 is configured to interface with a proximal edge 237 of the capsule 208. Thus, when a compressive force is applied to the capsule 208, the proximal edge 237 of the capsule 208 slides proximally along the ramped surface 256 of each of the fingers 252, causing the fingers 252 to yield (i.e., moving away from one another) to disengage the engaging features 254, 262. In one embodiment, as shown in FIG. 3, the coupler 206 includes a circumferential groove 272 and/or notches extending about an exterior 274 of the coupler 206 between distal and proximal portions thereof (e.g., along a portion of the coupler 206 between the plurality of fingers 252 and the plurality of arms 276 of the coupler 206). In this embodiment, when the fingers 252 are moved away from one another to release the capsule 208 therefrom, the fingers 252 may bend at the groove 272, causing the fingers 252 to snap away from the proximal portion including the arms 276. In another embodiment, as shown in FIG. 4, points at which fingers 252' contact a remaining portion (e.g., arms 276') of a coupler 206' may include longitudinal notches 272' so that when the fingers 252' are moved away from one another, the fingers 252' yield to release the capsule 208 by tearing along the longitudinal notches 272'.

To load the clip assembly 202 to the applicator 204, the catheter 210 may be moved distally relative to the capsule 208 (which is pre-assembled with the coupler 206) of the clip assembly 202 until the arms 276 of the coupler 206 are mounted over the distal end 260 of the catheter 210, as described above. In particular, the arms 276 of the coupler 206 deflect away from one another so that the distal end 260 of the catheter 210 may be received therebetween and tabs 250 engage a corresponding engaging feature of the catheter 210. The control member may then be moved longitudinally through the coupler 206 so that the enlarged distal end thereof may engage the yoke of the clip assembly 202. Once the control member is coupled to the yoke, loading of the clip assembly 202 is complete so that the clip assembly 202 may be inserted into a body to clip tissue, as desired.

The system 200 may be used to clip tissue in a manner substantially similar to the system 100, described above. Once tissue has been clipped, as desired and the clip assembly 202 is locked in a tissue clipping configuration, the clip assembly 202 may be deployed by drawing the control member proximally relative to the applicator 204. This proximal motion of the control member draws the entire clip assembly 202, including the capsule 208, proximally relative to the catheter 210, applying a compressive force thereto. As the capsule 208 is compressed against the coupler 206, the proximal edge 237 of the capsule 208 slides proximally against the ramped surface 256 of the fingers 252, causing the fingers 252 to deflect away from one another. As described above, the fingers 252 may yield by fracturing and/or tearing away from the proximal portion of the coupler 206. Yielding of the fingers 252 releases the capsule 208 from the applicator 204. A further proximal motion of the control member releases causes the control member to disengage the yoke of the clip assembly 202, leaving the clip assembly 202 clipped over the target tissue. Where the coupler 206 fractures to release the clip assembly 202, any portions of the coupler 206 that break off may be left in the body to pass naturally therethrough. Once the applicator 204 is removed from the body, if so desired, a new clip assembly 202 may be loaded onto the applicator 204 in the same manner as described above, so that the system 200 may be used to clip a second portion of tissue. This process may be repeated using the same applicator 204 as many times as needed or desired.

Figure 5:
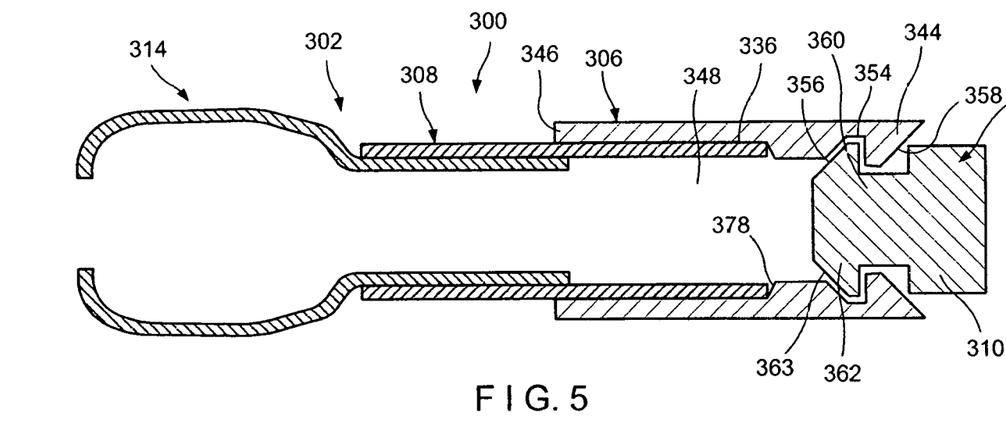
FIG. 5 shows a longitudinal cross-sectional view of a system according to yet another exemplary embodiment of the present disclosure.
Figure 6:
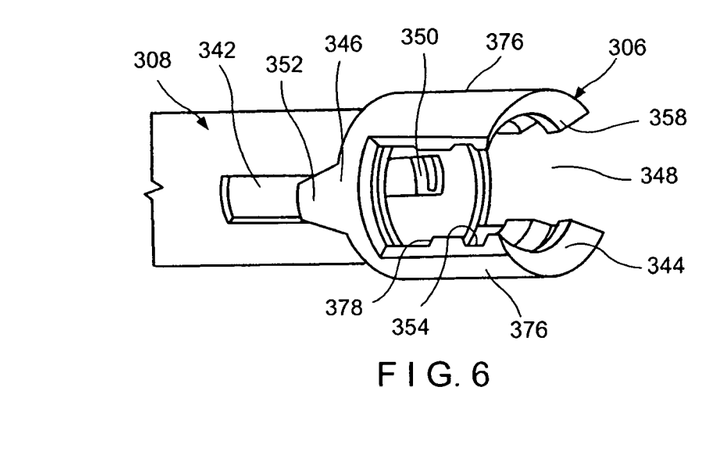
FIG. 6 shows a perspective view of a coupler assembled with a capsule according to the system of FIG. 5.

As shown in FIGS. 5-10, a system 300 according to yet another exemplary embodiment of the present disclosure is substantially similar to the systems 100 and 200 described above except as described below, comprising a clip assembly 302, an applicator 304 and a coupler 306 facilitating a releasable connection between the applicator 304 and the clip assembly 302. Similarly to the systems 100, 200, the coupler 306 may be pre-assembled with a capsule 308 of the clip assembly 302 and is configured to be releasably connected to a catheter 310 of the applicator 304. A control member (not shown) of the applicator 304 may be similarly coupled to clip arms 314 of the clip assembly 302 to move the clip assembly between an open, tissue receiving configuration, and a closed, tissue gripping configuration, as described above with respect to the systems 100, 200. Upon clipping of target tissue, as desired, a compressive force exerted on the coupler 306 causes a portion of the coupler 306 to yield to deploy the clip assembly 302 in a body over the target tissue. Rather than a fixed, snap-fit connection between the coupler 306 and the capsule 308, as described above with respect to the systems 100, 200, however, the coupler 306 and the capsule 308 are connected to one another via a sliding engagement, as shown in FIG. 6, to minimize a deployed length of the clip assembly 302. As will be understood by those of skill in the art, the minimized length of the clip assembly 302, in particular, the capsule 308, can reduce physical and visual obstructions during the procedure.

According to this embodiment, the coupler 306 extends from a proximal end 344 to a distal end 346 and includes a channel 348 extending therethrough. The distal end 346 of the coupler 306 may be mounted over a proximal end 336 of the capsule 308 to be pre-assembled therewith. The distal end 346 may include, for example, at least two distally extending fingers 352, distal ends of each including a tab 350 extending laterally inward to engage a corresponding elongated window 342 of the capsule 308. Elongated windows 342 are sized and shaped to permit the tabs 350 to slide longitudinally therealong. The fingers 352 of this embodiment are biased toward a first configuration, but configured to flex outward with respect to one another toward a second configuration to permit the coupler 306 to be mounted over the proximal end 336 of the capsule 308. Once the tabs 350 are received within the windows 342, however, the fingers 352 revert to their biased configuration, so that the tabs 350 engage the elongated windows 342. As described above, the coupler 306 may be pre-assembled with the capsule 308.

Figures 7, 8:
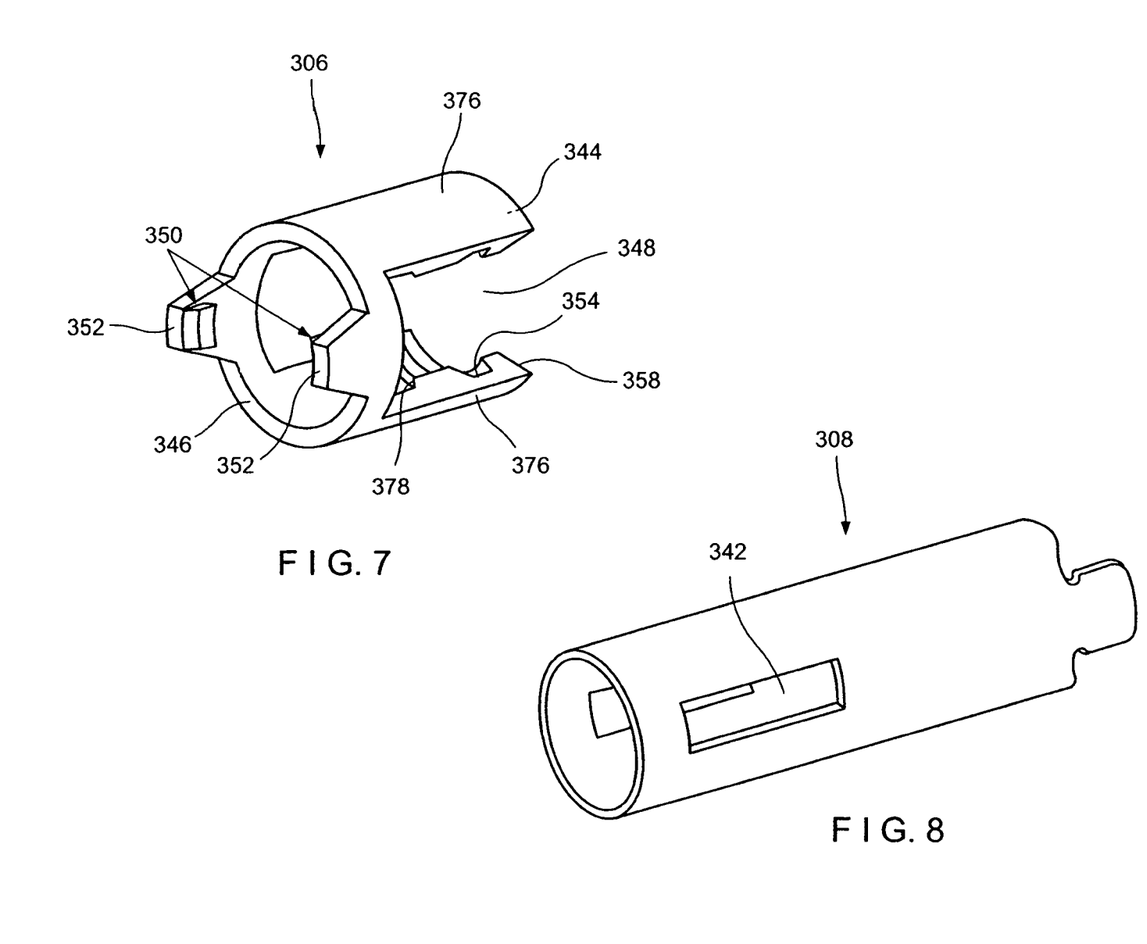
FIG. 7 shows the coupler of the system of FIG. 5.
FIG. 8 shows the capsule of the system of FIG. 5.

The proximal end 344 of the coupler 306 of this embodiment includes a plurality of deflectable arms 376 for coupling to a distal end 360 of the catheter 310 of the applicator 304. The deflectable arms 376 are mountable over the distal end 360 of the catheter 310 and each includes a groove 354 along a proximal portion thereof. The grooves 354 extend along an interior surface of each arm 376 and are sized and shaped to receive a corresponding engaging feature 362 at the distal end 360 of the catheter 310. The arms 376 deflect away from one another as the engaging feature 362 is received within the grooves 354. Once the engaging feature 362 has been received within the grooves 354, however, the deflectable arms 376 snap inward under their natural bias so that the grooves 354 engage the engaging feature 362. As will be described in further detail below, each of the grooves 354 includes a tapered surface 356 tapering toward a distal end thereof for interfacing with the engaging feature 362 when a compressive force is applied thereto, causing the coupler 306 to yield and allowing the catheter 310 to be released therefrom.

Distal of the grooves 354, each of the deflectable arms 376 may also include a shoulder 378 configured as a stop which, while the clip assembly 302 is moved from the open to the closed configuration, prevents the proximal end 336 of the capsule 308 from moving distally therepast. A proximal end of each of the deflectable arms 376 may also include an angled interior edge 358 tapering toward a distal end thereof to facilitate receipt of the engaging feature 362 between the deflectable arms 376.

The applicator 304 may be substantially similar to the applicators 104, 204 described above with respect to the systems 100, 200. A distal portion 368 of the catheter 310 is sized and shaped to be inserted between the deflectable arms 376 of the coupler 306 so that the engaging feature 362 engages the grooves 354. The engaging feature 362 may have any of a variety of configurations so long as the engaging feature 362 is engagable with the grooves 354 via a snap fit. In one embodiment, the engaging feature 362 comprises a plurality of tabs extending laterally outward (e.g., radially away from a longitudinal axis of the catheter 310) from the distal end 360. In another embodiment, the engaging feature may be configured as a radially outwardly extending protrusion extending about a periphery (e.g., circumference) of the distal end 360. The engaging feature 362 may include a tapered surface 363 tapering toward a distal end thereof for interfacing with the tapered surface 356 of the groove 354 of the coupler 306 during deployment of the clip assembly 302.

Similarly to the systems 100, 200, the pre-assembled clip assembly 302 and the coupler 306 may be housed within a cartridge, which holds the coupler 306 at a proximal-most position with respect to the clip assembly 302 during loading of the clip assembly 302 onto the applicator 304. The cartridge prevents the coupler 306 from being moved distally with respect to the clip assembly 302 during loading of the clip assembly 302 to the applicator 304.

During loading of the clip assembly, the distal end 360 of the catheter 310 is pushed distally against the proximal interior edge 358 of the coupler 306, causing the arms 376 to deflect radially outward so that the engaging feature 362 may be moved distally between the deflectable arms 376 into the grooves 354. Once the engaging feature 362 has been received within the grooves 354, the deflectable arms 376 revert to their biased configuration, snapping radially inward over the distal end 360 of the catheter 310. A control wire passing through the catheter is coupled to the clip arms 314 substantially as described above with respect to the system 100.

Figures 9, 10:
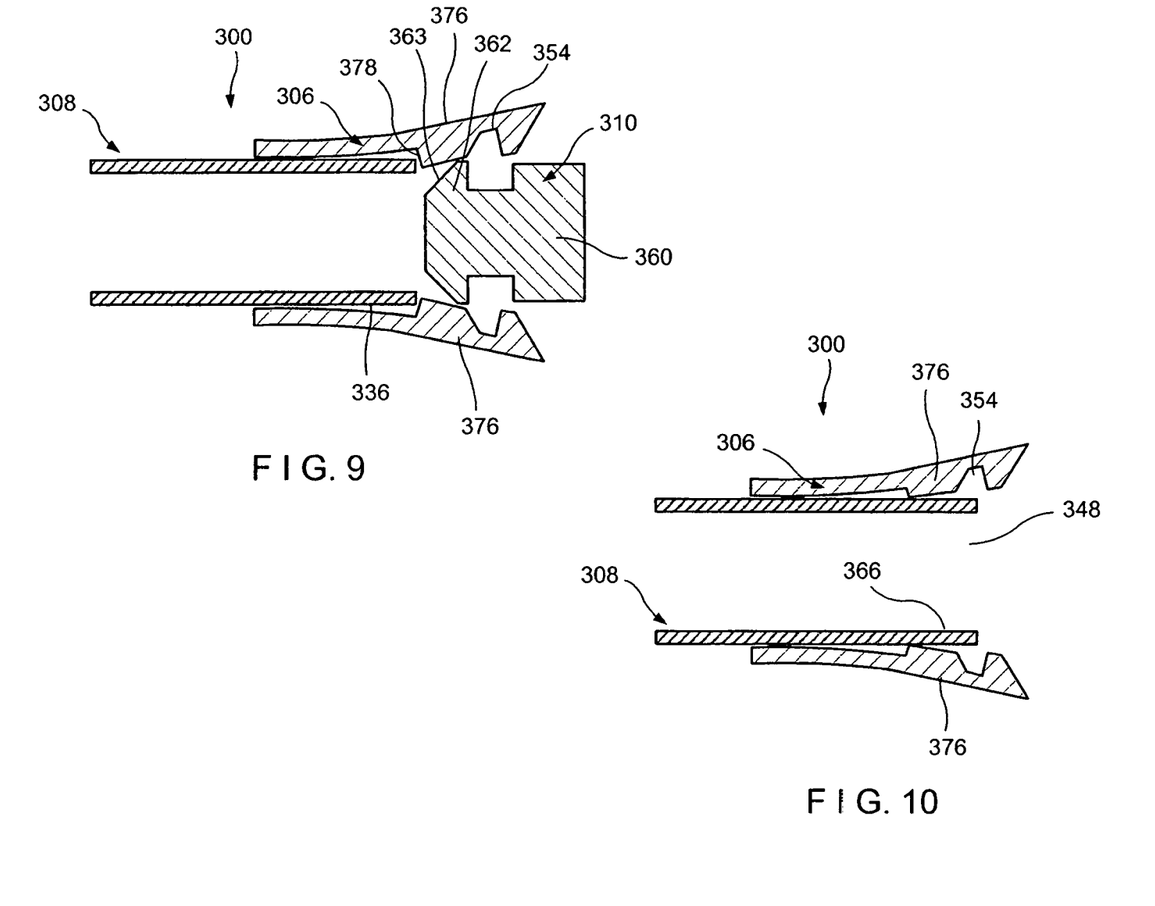
FIG. 9 shows a longitudinal cross-sectional view of a compressive force applied to the coupler during deployment of a clip assembly of the system of FIG. 5.
FIG. 10 shows a longitudinal cross-sectional view of the capsule being drawn proximally into the coupler during deployment of the clip assembly of the system of FIG. 5.

Upon loading of the clip assembly 302 onto the applicator 304, the clip assembly 302 may be moved between the open and closed configurations until target tissue has been gripped between the clip arms 314, as desired. Once the target tissue has been gripped as desired, the clip arms 314 are drawn further proximally (via the control wire) relative to the capsule 308 until the clip arms 314 are locked with respect to the capsule 308, as described above with respect to the systems 100, 200. Even further proximal motion of the control wire then causes the capsule 308 which is now locked relative to the clip arms 314, to be moved proximally relative to the coupler 306. In other words, the tabs 350 of the coupler 306 slide distally within the elongated window 342 until the proximal end 336 of the capsule 308 abuts the shoulder 378 of the coupler 306 and is prevented from moving proximally therepast. The proximal force of the capsule 308 against the coupler 306 applies compressive force to the coupler 306, causing the tapered surface 363 of the engaging feature 362 of the catheter 310 to interface with the tapered surfaces 356 of the grooves 354, thereby deflecting the arms 376 radially outward, as shown in FIG. 9. As the arms 376 are deflected outward, the proximal end 336 of the capsule 308 is simultaneously permitted to move proximally past the shoulder 378, as shown in FIG. 10, via a distal sliding of the tabs 350 within the elongated windows 342. As the capsule 308 is moved proximally with respect to the coupler 306, the arms 376 are maintained in a deflected configuration via an exterior surface of the capsule 308 so that the catheter 310 may be disengaged therefrom. Once the catheter 310 has been disengaged from the capsule 308, the control member is drawn even further proximally until the control member is disengaged from the clip arms 314 so that the entire applicator 304 may be withdrawn proximally from the body, leaving the clip assembly 302 (and the coupler 306 mounted thereover) clipped over the target tissue. Since the capsule 308 is drawn proximally into the channel 348 of the coupler 306 during deployment, a length of the deployed clip assembly 302 is minimized.

Figure 11:
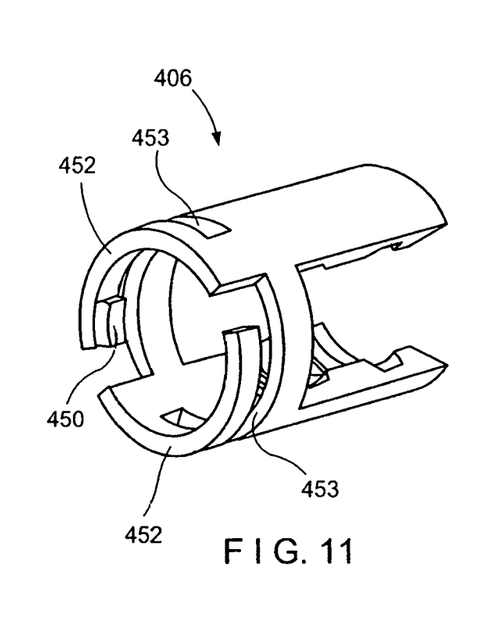
FIG. 11 shows a perspective view of a coupler according to an alternate embodiment of the present disclosure.

Although the system 300 described a coupler 306 having distally extending fingers 352 including tabs 350 for engaging the elongated window 342 of the capsule 308, those skilled in the art will understand that a coupler may include any of a variety of engaging structures or features for engaging the elongated window 342 of the capsule 308. According to an alternate embodiment, as shown in FIG. 11, a coupler 406 may be substantially similar to the coupler 306 and may be utilized with the clip assembly 302 and applicator 304 of the system 300. Fingers 452 of the coupler 406, however, do not extend distally from a distal end 446 of the coupler. Rather, the fingers 452 are defined via cut-outs 453 extending along the distal end 346 of the coupler 406 about a longitudinal axis of the coupler 406. For example, the coupler 406 may include two cut-outs 453, each of which extends partially about the distal end 446 to define a pair of fingers 452, each finger 452 configured as a curved prong extending about a portion of a diameter of the coupler 406. Each finger 452 includes a tab 450 extending radially inward from a tip of the prong to engage the elongated window 342 of the capsule 308 of the clip assembly 302. The curved prong configuration of the fingers 452 similarly permit a flexing of the fingers 452 during assembly of the coupler 406 with the capsule 308.

Figure 12:
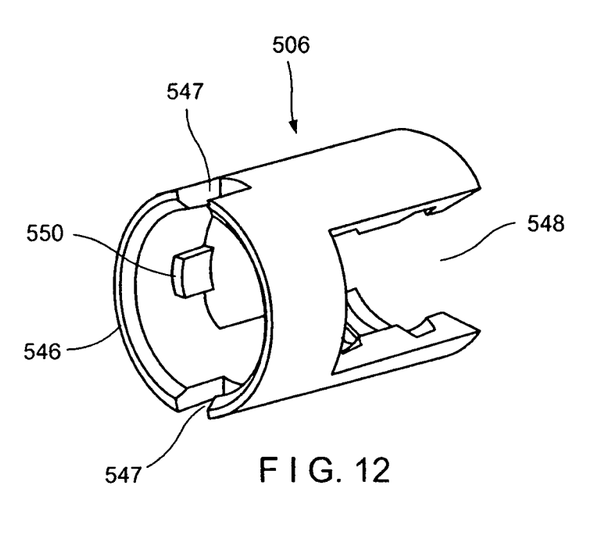
FIG. 12 shows a perspective view of a coupler according to yet another alternate embodiment of the present disclosure.
Figure 13:
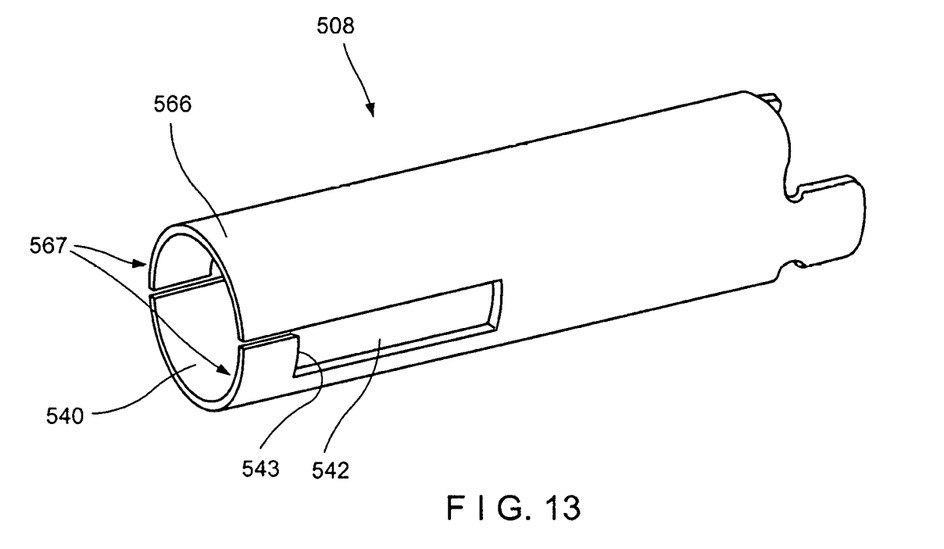
FIG. 13 shows a perspective view of a capsule for coupling to the coupler of FIG. 12.

According to yet another alternate embodiment, a coupler 506, as shown in FIG. 12, may be substantially similar to the couplers 306, 406 described above except as described below, and is configured to be assembled with a capsule 508, as shown in FIG. 13, which is substantially similar to the capsule 308 described above with respect to the system 300. Rather than including fingers which may be flexed away from a position toward which they are biased to engage an elongated window 542 of the capsule 508, an interior surface of a channel 548 of the coupler 506 may include a protrusion 550 extending into the channel 548 for engaging the elongated window 542. A distal end 546 of the coupler 506 may also include cut-outs 547 to allow a slight flexing of the distal end 546 to aid in mounting of the coupler 506 over a proximal end 566 of the capsule 508. The proximal end 566 of the capsule 508 includes a tab 567 which defines a proximal end 543 of the elongated window 542 and which may be crimped radially inward into a channel 540 of the capsule 508. Upon crimping of the tab 567, the coupler 506 may be mounted over the proximal end 566 of the capsule 508 so that the protrusion 540 along the interior surface of the channel 548 of the coupler 506 may be slid distally into the elongated window 542. Once the protrusion 550 has been received within the elongated window 542, the tab 567 may be moved back to its initial position so that the protrusion 550 is locked within the elongated window 542.

It is noted that although the exemplary embodiment describes a single protrusion 550, the coupler 506 may include any number of protrusions 550 and, in a particular embodiment, may include a pair of protrusions 550, each of which are diametrically opposed from one another along the interior surface of the channel 540 of the coupler 506. Thus, each of the protrusions 550 may be received within a corresponding one of a pair of elongated windows 542 of the capsule 508, the proximal end 566 of the capsule 508 including a pair of tabs 567 defining proximal ends 543 of the elongated windows 542.

It will be apparent to those skilled in the art that various modifications may be made in the present disclosure, without departing from the scope of the disclosure.

What is claimed is:

1. A system for treating tissue, comprising:
a first clip assembly including a pair of first clip arms, each of the first clip arms extending from a proximal end to a distal end, proximal ends of the first clip arms slidably received within a channel of a first capsule to be moved between a tissue receiving configuration, in which distal ends of the first clip arms are separated from one another, and a tissue clipping configuration, in which distal ends of the first clip arms are moved toward one another;
a second clip assembly including a pair of second clip arms, each of the second clip arms extending from a proximal end to a distal end, proximal ends of the second clip arms slidably received within a channel of a second capsule to be moved between a tissue receiving configuration, in which distal ends of the second clip arms are separated from one another, and a tissue clipping configuration, in which distal ends of the second clip arms are moved toward one another;

an applicator including a catheter and a control member extending therethrough, the control member including a distal end configured to be connected to the first clip assembly to move the first clip assembly between the tissue receiving configuration and the tissue clipping configuration; and a first coupler attached to one of a proximal end of the first capsule and a distal end of the catheter of the applicator, the first coupler being configured to releasably couple the first clip assembly and the catheter to one another so that, after the first clip assembly has been deployed from the applicator, the second clip assembly can be connected to the distal end of the control member to move the second clip assembly between the tissue receiving configuration and the tissue clipping configuration and a second coupler can be attached to one of a proximal end of the capsule of the second clip assembly and the distal end of the catheter of the applicator.

2. The system of claim 1, wherein the proximal ends of the first clip arms are connected to one another via a yoke releasably coupleable with an enlarged distal end of the control member.

3. The system of claim 1, wherein the coupler is attached to the proximal end of the first capsule and a proximal portion of the first coupler includes a plurality of arms mountable over a distal portion of the catheter to be releasably coupled thereto, the arms of the first coupler being movable between a biased engaging configuration and a non-engaging configuration, in which the arms of the first coupler are deflected away from a longitudinal axis of the first coupler.

4. The system of claim 3, wherein each of the arms of the first coupler includes a groove extending along an interior surface thereof, the groove sized and shaped to receive a correspondingly sized and shaped tab extending outwardly laterally away from the distal end of the catheter.

5. The system of claim 4, wherein each of the grooves includes a tapered surface tapering toward a distal end thereof so that when a compressive force is applied to the first coupler, the tab of the catheter slides distally along the tapered surface of the groove to deflect the arms of the first coupler away from the longitudinal axis of the first coupler.

6. The system of claim 3, wherein a proximal interior edge of each of the arms of the first coupler is angled.

7. The system of claim 6, wherein the catheter includes a shoulder extending along a portion thereof for interfacing with the proximal edge of the arms to deflect the arms of the first coupler away from the longitudinal axis.

8. The system of claim 3, wherein the first coupler further includes a plurality of fingers coupled to the proximal end of the first capsule, a distal end of each of the fingers of the first coupler including a tab extending radially inward to engage a correspondingly sized and shaped window extending laterally through a wall of the proximal portion of the first capsule.

9. The system of claim 8, wherein the window of the first capsule is elongated to permit a longitudinal sliding of the first coupler relative to the first capsule.

10. The system of claim 8, wherein an interior surface of each of the fingers of the first coupler includes a ramped surface tapering toward a proximal end thereof so that when a compressive force is applied thereto, the fingers of the first coupler deflect away from a longitudinal axis of the first coupler.

11. The system of claim 1, wherein the first clip arms include gripping features configured to grip the tissue therebetween.

12. The system of claim 1, wherein at least one of the first clip arms includes a locking tab extending laterally outward therefrom configured to engage a portion of the first capsule when the first clip arms have been drawn into the first capsule by a predetermined distance.

* * * * *